US010421785B2

(12) United States Patent
Yadid et al.

(10) Patent No.: US 10,421,785 B2
(45) Date of Patent: Sep. 24, 2019

(54) DELTA RECEPTOR AGONIST PEPTIDES AND USE THEREOF

(71) Applicants: BAR-ILAN UNIVERSITY, Ramat Gan (IL); ARIEL SCIENTIFIC INNOVATIONS LTD., Ariel (IL)

(72) Inventors: Gal Yadid, Shoham (IL); Michael Firer, Karnei Shomron (IL); Rachela Popovtzer, Givat Shmuel (IL)

(73) Assignees: BAR-ILAN UNIVERSITY, Ramat Gan (IL); ARIEL SCIENTIFIC INNOVATIONS LTD., Ariel (IL)

( * ) Notice: Subject to any disclaimer, the term of this patent is extended or adjusted under 35 U.S.C. 154(b) by 37 days.

(21) Appl. No.: 15/482,846

(22) Filed: Apr. 10, 2017

(65) Prior Publication Data

US 2017/0291922 A1    Oct. 12, 2017

Related U.S. Application Data

(60) Provisional application No. 62/320,638, filed on Apr. 11, 2016.

(51) Int. Cl.
```
C07K 7/00      (2006.01)
A61K 38/16     (2006.01)
C07K 7/08      (2006.01)
A61K 38/10     (2006.01)
C07K 14/665    (2006.01)
A61K 9/51      (2006.01)
A61K 47/52     (2017.01)
A61K 47/69     (2017.01)
A61K 38/00     (2006.01)
```

(52) U.S. Cl.
CPC ............. *C07K 7/08* (2013.01); *A61K 9/5146* (2013.01); *A61K 38/10* (2013.01); *A61K 47/52* (2017.08); *A61K 47/6923* (2017.08); *A61K 47/6929* (2017.08); *A61K 47/6935* (2017.08); *C07K 14/665* (2013.01); *A61K 38/00* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs et al. |
| 3,850,572 A | 11/1974 | Andrus |
| 3,850,578 A | 11/1974 | McConnell |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,661,913 A | 4/1987 | Wu et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,446,090 A | 8/1995 | Harris |
| 5,880,255 A | 3/1999 | Delgado et al. |
| 6,113,906 A | 9/2000 | Greenwald et al. |

OTHER PUBLICATIONS

Befort et al., "Effects of delta opioid receptors activation on a response inhibition task in rats", Psychopharmacology, (2011) 214: 967-976.

JF Dalayeun et al., "Physiology of beta-endorphins. A close-up view and a review of the literature" Biomed Pharmacother (1993) 47, 311-320.

Herman Friedman et al., "Neurological basis of drug dependence and its effects on the immune system", Journal of Neuroimmunology 147 (2004) 106-108.

Yuliya Georgieva et al., "Design and screening of M13 phage display cDNA libraries" Molecules (2011), 16, 1667-1681.

Hipolito Lucia et al., "Shell/core differences in mu- and delta-opioid receptor modulation of dopamine efflux in nucleus accumbens", Neuropharmacology 55 (2008): 183-189.

Begonia Y. Ho et al., "Determination of delta-opioid in NG108-15 cells", European Journal of Pharmacology 319 1997 109-114.

George F. Koob et al., "Drug Addiction, Dysregulation of Reward, and Allostasis", Neuropsychopharmacology (2001) 24(2): 97-129.

J,. Kowalski et al., "Immunomodulatory action of class mu-, delta- and kappa-opioid receptor agonists in mice", Neuropeptides (1998) 32(4): 301-306.

Edward L. Morgan et al., "Regulation of human B lymphocyte activation by opioid peptide hormones. Inhibition of IgG production by opioid receptor class (mu-, kappa-, and delta-) selective agonists", Journal Neuroimmunol 65(1996): 21-30.

Yuliia N. Nekrasova et al., "Binding of synthetic peptide TPLVTLFK to nonopioid beta-endorphin receptor on rat brain membranes", Journal Peptide Science (2010) 16(6): 263-268.

Shane A. Perrine et al., "Delta opioid receptor ligands modulate anxiety-like behaviors in the rat", British Journal of Pharmacology (2006) 147(8): 864-872.

Sue L. Povlock et al., "A multisubstrate kinetic mechanism of dopamine transport in the nucleus accumbens and its inhibition by cocaine", Journal of Neurochemistry (1997) 69(3): 1093-1105.

(Continued)

*Primary Examiner* — Michael D Pak

(74) *Attorney, Agent, or Firm* — The Roy Gross Law Firm, LLC; Roy Gross

(57) ABSTRACT

Peptides effective as delta opioid receptor agonists and compositions comprising same are provided. Further provided are methods for targeting medical conditions amenable to treatment with an opioid receptor agonist, including but not limited to, conditions involving pain as well as reducing cocaine craving.

14 Claims, 9 Drawing Sheets

Specification includes a Sequence Listing.

(56) References Cited

OTHER PUBLICATIONS

Ilana Roth-Deri et al., "Beta-endorphin and drug-induced reward and reinforcement", Progress in Neurobiology 86 (2008) 1-21.
Diana Simmons et al., "Role of mu- and delta-opioid receptors in the nucleus accumbens in cocaine-seeking behavior", Neuropsychopharmacology (2009) 34(8): 1946-1957.
M.J. Przydzial et al, "Roles of residues 3 and 4 in cyclic tetrapeptide ligand recognition by the K-opioid receptor", J. Peptide Res. 65, 2005 / 333-342.
Gianfranco Balboni et al., "Synthesis and Opioid Activity of N,N-Dimethyl-Dmt-Tic-NH-CH(R)-R' Analogues: Acquisition of Potent delta Antagonism", Bioorganic & Medicinal Chemistry 11 (2003) 5435-5441.
Gianfranco Balboni et al., "Potent delta-Opioid Receptor Agonists Containing the Dmt-Tic Pharmacophore" J. Med. Chem. 2002, 45, 5556-5563.
L. H. Lazarus et al., "Function of Negative Charge in the "Address Domain" of Deltorphins"., J. Med. Chem. (1991), 34, 1350-1355.
Severo Salvadori et al., "Further Studies on the Dmt-Tic Pharmacophore: Hydrophobic Substituents at the C-Terminus Endow delta Antagonists to Manifest mu Agonism or mu Antagonism", J. Med. Chem. 1999, 42, 5010-5019.
Jonathan D. Cechetto et al., "Immunoelectron Microscopy Provides Evidence That Tumor Necrosis Factor Receptor-Associated Protein 1 (TRAP-1) Is a Mitochondrial Protein Which also Localizes at Specific Extramitochondrial Sites", Experimental Cell Research (2000) 260, 30-39.

Day 1

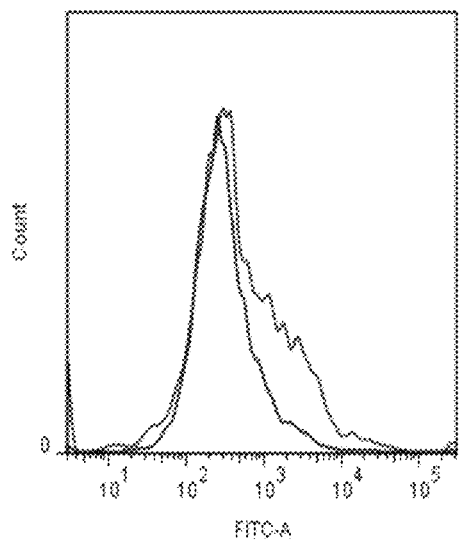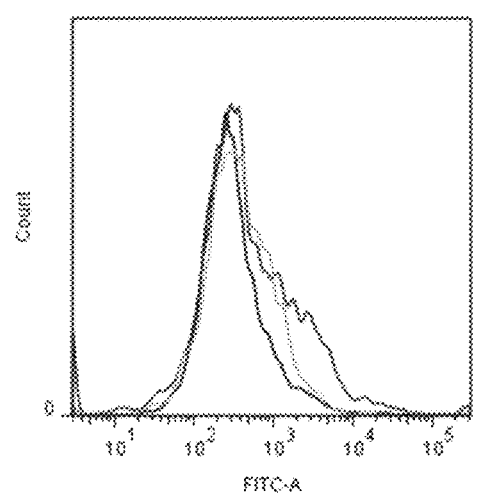
Figure 9A
Figure 9B
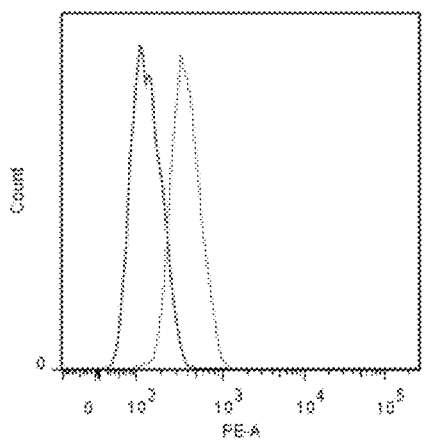
Figure 10

SEQUENCE LISTING

```
<160> NUMBER OF SEQ ID NOS: 2

<210> SEQ ID NO 1
<211> LENGTH: 12
<212> TYPE: PRT
<213> ORGANISM: artificial sequence
<220> FEATURE:
<223> OTHER INFORMATION: Synthetic peptide

<400> SEQUENCE: 1

Ile Ile Ala Gly Glu Tyr Lys Gln Met Leu Thr Leu
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2

Asn Gly Asn Asp Arg Thr Asp Gln Met Pro Leu Pro
1               5                   10
```

DELTA RECEPTOR AGONIST PEPTIDES AND USE THEREOF

FIELD OF INVENTION

The present invention is directed, inter alia, to delta receptor agonist peptides and use thereof.

BACKGROUND OF THE INVENTION

Drug addiction is defined as an urge to consume the same drug repeatedly and development of drug dependence. Usually drug addiction is accompanied by development of tolerance to the addictive substance leading to heighten craving, and it becomes necessary to increase the dose of the substance in order to reach the desired effect of the drug. When the user stops taking the drug, he develops withdrawal symptoms that can include mental disorders and severe physical pain. Drug abuse is a global problem and each year drug use-related deaths occur, mainly due to repeated exposure to the drug and drug addiction effects on brain function. Neuropsychotic drugs causes changes in behavior and physiology which might differ depending on the amount of the drug that reaches a specific region of the brain and the release and function of various neurotransmitters that are affected by the drug. Despite the differences between the addictive substances, they all have in common an impact on the reward system in the brain.

Cocaine addiction poses a serious problem to society. Countless deaths occur worldwide as a result of cocaine abuse, levels of which are on the rise. Cocaine craving, induced by drug-associated environmental cues, intensifies or "incubates" over the first few weeks of abstinence, and persists over extended periods of time. As a result, addicts are prone to relapse even after long durations of abstinence. Grimm et al. first demonstrated an analogous incubation phenomenon in rats, in which onset of craving is delayed and craving does not decay, but rather progressively increases over a prolonged period of forced abstinence. According to this model, this time-dependent increase can be modeled. By exposing the rats to intensive training, the researchers showed that cocaine seeking, induced by re-exposure to drug-associated cues, progressively increases over the first two months after withdrawal from cocaine self-administration. This unique phenomenon was called: "the incubation of cocaine craving" and it was investigated by many researchers.

Endogenous opioids stimulate receptors that cause analgesia and reduce pain. Research has distinguished between the mu (μ) opioid type receptor which is stimulated by morphine, the kappa (κ) type which binds ketocyclazocine and the delta (δ) type, which was discovered later. Endogenous opioids bind with different affinities to different kinds of opioid receptors. Most endogenous opioids are derived from three pre-proteins: PDYN, PENK and POMC (pro-opiomelanocortin).

Enzymatic processing of POMC generates β-lipotrophin, cleaved to produce β-endorphin, an endogenous opioid peptide consisting of 31 amino acids. β-endorphin binds at high affinity to the mu and delta opioid receptors (MOR and DOR), while its affinity to kappa opioid receptor (KOR) is lower. As a neurotransmitter in the central nervous system, it is involved in relief of stress and pain, processes of learning and memory, and mediating the rewarding effects of substances of abuse. However, as β-endorphin does not cross the blood-brain barrier (BBB), it can therefore only be given by direct injection to the brain, significantly restricting its clinical application.

New modalities providing safe and effective treatment of cocaine addiction have not appeared despite much effort. There is a need for delta receptor ligands that would both mimic the cocaine craving-reducing effects of β-endorphin and would also be candidates for use in drug rehabilitation therapy. Further, there is a need for highly specific delta receptor agonist that will act as analgesic drugs.

SUMMARY OF THE INVENTION

The present invention provides peptides effective as selective delta opioid receptor agonists and compositions comprising same. The present invention further provides methods for targeting medical conditions amenable to treatment with an opioid receptor agonist, including but not limited to, conditions involving pain as well as reducing cocaine craving.

According to one aspect, the present invention provides an isolated polypeptide of less than 30 amino acid residues comprising an amino acid sequence as set forth in any one of:

SEQ ID NO: 1 (IIAGEYKQMLTL);
SEQ ID NO: 2 (NGNDRTDQMPLP);
or an analog, a derivative or fragment thereof.

According to some embodiments, said peptide has a length of no more than 25 amino acids. According to some embodiments, said peptide has a length of no more than 20 amino acids.

According to some embodiments, said analog, derivative or fragment of said peptide has at least 80% sequence identity to SEQ ID NO: 1. According to some embodiments, said analog, derivative or fragment of said peptide has at least 80% sequence identity to SEQ ID NO: 2.

According to some embodiments, said peptide has a high binding affinity to delta (δ) opioid receptor. According to some embodiments, said peptide has an increased binding affinity to delta (δ) opioid receptor.

According to another aspect, the present invention provides a pharmaceutical composition comprising as an active ingredient a pharmaceutically acceptable amount of an isolated polypeptide of the present invention, and a pharmaceutically acceptable carrier.

According to some embodiments, said compositions comprise a particle. According to some embodiments, said particle is a gold nanoparticle (GNP). According to some embodiments, said GNP is a PEGylated GNP.

According to some embodiments, said peptide may be modified so as to enhance cellular uptake. According to some embodiments, said peptide may be modified so as to enhance BBB penetration. According to some embodiments, said peptide may be modified with a polymer (e.g., a hydrophilic polymer including but not limited to polyethylene glycol). According to some embodiments, said modified peptide is a cyclized peptide.

According to some embodiments, said peptide is directly attached (linked) to said particle (e.g., GNP). According to some embodiments, said peptide is linked to said particle via a functional group (such as, PEG). In some embodiments, said linkage is by a covalent bond.

According to another aspect, the present invention provides a method of treating or ameliorating a medical condition amenable to treatment with an opioid receptor agonist, the method comprising administering to a subject in need thereof the pharmaceutical composition of the present invention, thereby treating said medical condition in said subject. According to some embodiments, said opioid receptor agonist is a delta opioid receptor agonist.

According to some embodiments, said medical condition is a substance abuse addiction. According to some embodiments, said substance is cocaine or a derivative thereof.

According to some embodiments, said medical condition is pain. Non-limiting examples of pain include acute pain, chronic pain, cancer pain, central pain, labor pain, myocardial infarction pain, pancreatic pain, colic pain, post-operative pain, headache pain, muscle pain, pain associated with intensive care, arthritic pain, neuropathic pain, and pain associated with an oral or periodontal disease, including gingivitis and periodontitis.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3A. The phage library was sequentially absorbed on non-target expressing cells to remove phage clones that bound non-relevant membrane components. Phage were incubated twice with each cell type. After absorption on each cell type, a small aliquot of the collected supernatant was used for titration and the remainder transferred to the next cell type. FIG. 3B. Analysis of opioid expression on C6 cells. Cells were incubated with either rabbit anti-delta-opioid receptor or rabbit anti-mu-opioid receptor and then goat anti-rabbit IgG-FITC. Fluorescent binding was measured by flow cytometry. The blank curves represent control (no primary antibody). To validate the receptor binding capability of the C6 binding clones, a mixture of $10^8$ phage particles and 0, 1, 10 or 100 nM of either the δ-opioid receptor agonist DSLET (3C) or μ-opioid receptor agonist DAMGO (3D) were added to the C6 cells. The presence of bound phage was evaluated by ELISA. The results shown are the means+/− standard deviation of three independent experiments. FIG. 3E. Calibration of DSLET-FITC and DAMGO-FITC on C6 cells. Prior to testing the inhibitory capacity of Peptide 1 and 2, 1, 2, 5 and 7 nM of the δ-opioid receptor agonist DSLET-FITC or 1, 2 and 5 nM of μ-opioid receptor agonist DAMGO-FITC were incubated with C6 cells. After washing, fluorescent binding was assessed by flow cytometry.

FIGS. 9A-B. FACS display of DOR and MOR binding to the C6 cells. (9A) DOR expression of the C6 cells demonstrated more expression than the control vehicle. (9B) DOR expression of the C6 cells is higher among the DOR than MOR and vehicle.

FIG. 10. FACS display of peptide 1 conjugated to gold nanoparticles binding to the delta opioid receptor expressed by the C6 cells, compared to C6 cells only. DOR attached cells showed higher affinity and exhibited better binding to the cells relative to vehicle.

DETAILED DESCRIPTION OF THE INVENTION

Figure 1A:
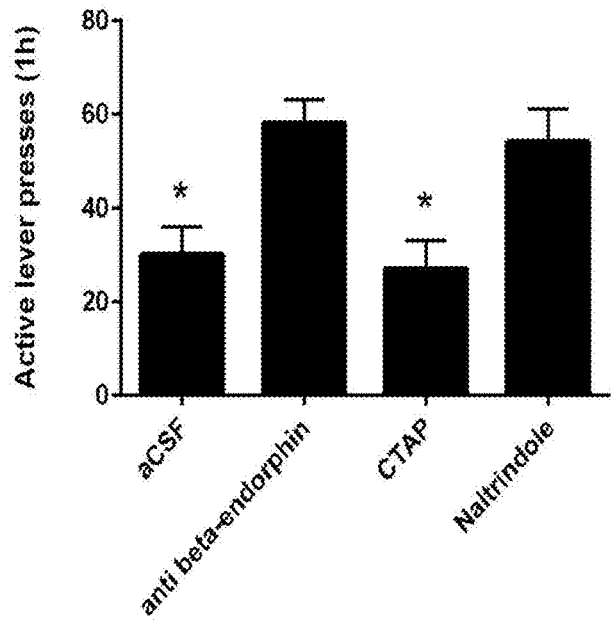
FIGS. 1A-B. Effect of intra-*Nucleus accumbens* (NAc) injection of δ or μ antagonist on cue-induced cocaine-seeking behavior after 1 day (1A) or 30 days (1B) of forced abstinence. Both intra-NAc infusions of the δ opioid receptor antagonist naltrindole (1 μg) on day 1, and naltrindole together with β-endorphin on day 30, increased cue-induced cocaine-seeking behavior. Intra-NAc injection of the μ opioid receptor antagonist CTAP (3 μg and 30 ng) had no behavioral effect. The results demonstrate a therapeutic effect for β-endorphin which is mediated specifically by the delta opioid receptor and not by the mu opioid receptor. N=9 per group.

The present invention provides peptides effective as delta opioid receptor agonists and compositions comprising same. The present invention further provides methods for targeting medical conditions amenable to treatment with an opioid receptor agonist, including but not limited to, conditions involving pain as well as reducing cocaine craving.

The present invention is based, in part, on the finding of novel peptides which demonstrate increased specificity for the δ-opioid receptor and function as receptor agonists. When conjugated to nanoparticles, these peptides were delivered to the *Nucleus accumbens* (NAc) region of the rat brain and were able to eliminate cocaine craving in a rat model of cocaine addiction.

According to some embodiments, the present invention provides an isolated polypeptide comprising an amino acid sequence as set forth in SEQ ID NO: 1 (IIAGEYKQMLTL), or an analog, a derivative or fragment thereof.

According to some embodiments, the present invention provides an isolated polypeptide comprising an amino acid sequence as set forth in SEQ ID NO: 2 (NGNDRTDQMPLP), or an analog, a derivative or fragment thereof.

According to some embodiments, said analog, derivative or fragment of said peptide has at least 80%, has at least 85%, has at least 90%, has at least 95% sequence identity to SEQ ID NO: 1.

According to some embodiments, said analog, derivative or fragment of said peptide has at least 80%, has at least 85%, has at least 90%, has at least 95% sequence identity to SEQ ID NO: 2.

According to some embodiments, said peptide has an increased binding affinity and/or specificity to delta (δ) opioid receptor. Methods of determining binding affinity, such as, binding affinity and/or specificity to delta (δ) opioid receptor are demonstrated herein below and are known to one skilled in the art.

In some embodiments in connection with selective binding affinity, "increased binding" or "substantially greater" means at least a two-fold, at least a three-fold, at least a four-fold, at least a five-fold, at least a six fold, at least a seven-fold, at least eight-fold, at least a nine-fold, at least a ten-fold, at least a fifteen-fold, at least a twenty-fold, at least a thirty-fold, at least a forty-fold, at least a fifty-fold or at least a hundred-fold increase in the amount of peptide bound to a receptor, such as compared to a non-delta opioid receptor.

According to some embodiments, said peptide binds to the delta opioid receptor with an IC50 of no more than 100 nM, no more than 50 nM or no more than 30 nM.

Binding affinity may be measured using any suitable technique, such as the competitive binding assays described in the Example; Przydzial et al., J. Pept. Res. 2005; 65(3): 333-42; Balboni et al., J. Med. Chem. 2002; 45:5556-5563; Lazarus et al., J. Med. Chem. 1991; 34:1350-1359; Salvadori et al., J. Med. Chem. 1999; 42:5010-5019; and Balboni et al., Bioorg. Med. Chem. 2003; 11:5435-5441. Alternative techniques for evaluating binding to the mu and delta opioid receptors (MOR and DOR, respectively), include, for example, flow cytometry, immunofluorescence microscopy, immunoelectron microscopy, and confocal laser microscopy. See, for example, U.S. Pat. No. 4,661,913, and Cechetto et al., Exp Cell Res. 2000; 260:30-39.

In some embodiments, the invention provides a method of detecting opioid receptor selected form MOR and DOR in a biological sample, the method comprising contacting the sample with the peptide described herein and detecting binding of the compound to MOR and/or DOR in the sample. In various embodiments, the method comprises exposing the sample to the peptide, washing excess peptide from the sample, and determining the presence or absence of the peptide bound to MOR and/or DOR. Optionally, the compound is conjugated to a detection moiety (e.g., marker protein, radiolabel, fluorescent compound and the like) to facilitate detection of the compound.

The terms "peptide" and "protein" are used interchangeably herein to refer to a sequence of amino acid residues. The terms also apply to amino acid sequences in which one or more amino acid residues is an artificial chemical analogue of a corresponding naturally occurring amino acid, as well as to naturally occurring amino acid polymers.

In some embodiments, the peptide is an isolated peptide. The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly-purified form, i.e., at least about 80% pure, at least about 90% pure, at least about 95% pure, greater than 95% pure, or greater than 99% pure.

The present invention further provides fragments, analogs and chemical modifications of the peptides of the present invention as long as they are capable of targeting δ-opioid receptor, and particularly act as δ-opioid agonists.

The term "selective agonists of delta-opioid receptors" or "selective delta-opioid receptor agonists" as used herein denotes any compound which has a higher binding affinity for the delta-opioid receptor than for any other opioid receptor. In particular, the term denotes agonist compounds capable of ligand-receptor binding to at least one opioid receptor, the agonist compound having a higher binding affinity for the delta-opioid receptor than for any other receptor normally found in the vicinity of the delta-opioid receptor in the human or animal body.

The term "agonist" as used herein refers to a drug which binds to a receptor and activates it, producing a pharmacological response (contraction, relaxation, secretion, enzyme activation, etc.).

The term "antagonist" as used herein refers to a drug which attenuates the effect of an agonist. It may be competitive (or surmountable), i.e. it binds reversibly to a region of the receptor in common with an agonist, but occupies the site without activating the effector mechanism. The effects of a competitive antagonist may be overcome by increasing the concentration of agonist, thereby shifting the equilibrium and increasing the proportion of receptors which the agonist occupies. However, it is now known that certain antagonists can affect receptor trafficking and therefore improve agonist actions indirectly.

In another embodiment, said peptide has a length of no more than 30 amino acids, no more than 29 amino acids, no more than 28 amino acids, no more than 27 amino acids, no more than 26 amino acids, no more than 25 amino acids, no more than 24 amino acids, no more than 23 amino acids, no more than 22 amino acids, no more than 21 amino acids, no more than 20 amino acids, no more than 19 amino acids, no more than 18 amino acids, no more than 17 amino acids, no more than 16, no more than 15 amino acids, no more than 14 amino acids, no more than 13 amino acids, or no more than 12 amino acids. Each possibility represents a separate embodiment of the present invention.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of targeting and binding delta (δ) opioid receptor, as specified herein.

The term "derived from" or "corresponding to" refers to construction of a peptide based on the knowledge of a sequence using any one of the suitable means known to one skilled in the art, e.g. chemical synthesis in accordance with standard protocols in the art.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C (R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of binding delta (δ) opioid receptor, as specified herein.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid.

The peptides of the invention may be synthesized or prepared by techniques well known in the art. The peptides can be synthesized by a solid phase peptide synthesis method of Merrifield (see J. Am. Chem. Soc, 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5 dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives, or analogs thereof joined at their amino or carboxy-terminus or at one of the side chains, such as via a peptide bond to an amino acid sequence corresponding to or derived from a different protein.

Additionally or alternatively, the peptides of the present invention, derivatives, or analogs thereof can be joined to another moiety such as, for example, a fatty acid, a sugar moiety, and a nucleic acid. Additionally or alternatively, the peptides of the present invention, derivatives, or analogs thereof can be joined to a tagging moiety such as, for example, a gold nanoparticle, a fluorophore, a chromophore, a chemilluminescent molecule, a magnetic particle, a dye or a radioactive isotope. Additionally or alternatively, the peptides of the present invention, derivatives, or analogs thereof can be joined to a drug, such as a cytotoxic drug. According to said embodiment, said peptide linked to a drug is specifically targeted to cell expressing delta opioid receptors.

As used herein, the term "drug" refers to pharmacologically active molecules that are used to diagnose, treat, or prevent diseases or pathological conditions in a physiological system (e.g., a subject, or in vivo, in vitro, or ex vivo cells, tissues, and organs).

Conjugates comprising peptides of the invention and a protein can be made by protein synthesis, e. g., by use of a peptide synthesizer, or by ligating the appropriate nucleic acid sequences encoding the desired amino acid sequences to each other by methods known in the art, in the proper coding frame, and expressing the conjugate by methods commonly known in the art.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

According to some embodiments, said peptide may be modified so as to enhance cellular uptake and/or facilitate transport of the peptide across the blood-brain barrier.

According to some embodiments, said modified peptide is a cyclized peptide. The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid residue having its carboxyl group and other reactive groups protected and the free primary carboxyl group of another amino acid residue having its amino group or other reactive groups protected. Any of a number of well-known procedures utilizing a variety of resins and reagents (e.g., by solid phase synthesis) may be used to prepare the cyclic peptides of the present invention. The process for synthesizing the cyclic peptides may be carried out by a procedure whereby each amino acid residue in the desired sequence is added one at a time in succession to another amino acid residue or by a procedure whereby peptide fragments with the desired amino acid sequence are first synthesized conventionally and then condensed to provide the desired peptide. The resulting peptide is then cyclized to yield a cyclic peptide of the invention.

According to some embodiments, said peptide is linked to a polymer. According to some embodiments, said peptide may be modified with a hydrophilic polymer (e.g., a process generally known as "pegylation") such as polyethylene glycol, chemically bound to one or more amino acids.

The term "hydrophilic polymer" refers to any water-soluble linear or branched polymer including, but not limited to, polyethylene glycol and polypropylene glycol and similar linear and branched polymers. In some embodiments, the molecular weight of the polymer ranges from about 500 daltons to about 50,000 daltons. Hydrophilic polymers for use in the invention typically have a reactive group incorporated for attachment to the peptide of the invention through amino, carboxyl, sulfhydryl, phosphate or hydroxyl functions.

Hydrophilic polymers used in the present invention, such as polyethylene glycol, can be prepared according to standard protocols with one end capped as with a methoxy group and the other end activated for facile conjugation, to active groups on bioactive molecules. For anon-limiting example, U.S. Pat. No. 6,113,906 describes the use of succinamidyl succinate or carbamate reactive groups on the polyethylene glycol to react with amine groups on proteins. U.S. Pat. No. 5,446,090 describes the use of sulfone derivatives of polyethylene glycol to form stable bonds with sulfhydryl groups of proteins. U.S. Pat. No. 5,880,255 describes the use of tresyl derivatives for reaction at amine groups of proteins to form a simple, stable secondary amine linkage.

Gold Nanoparticles

According to some embodiments, the peptide of the present invention (e.g., SEQ ID NO: 1 or 2) is conjugated to a particle. In one embodiment, said particle facilitates transport of the peptide of the invention across the blood-brain barrier.

According to some embodiments, said particle is a nanoparticle. In some embodiments, the nanoparticle has a particle size up to 100 nm, or alternatively up to 50 nm, or alternatively up to 40 nm, or alternatively up to 35 nm, or alternatively up to 30 nm, or alternatively up to 25 nm, or alternatively up to 20 nm. In other embodiments, the nanoparticle has a particle size greater than 5 nm, or alternatively greater than 10 nm, or alternatively greater than 20 nm, or alternatively greater than 30 nm, or alternatively greater than 35 nm, or alternatively greater than 40 nm. Each possibility represents a separate embodiment of the present invention.

In some embodiments, the particle is a metal such as a heavy metal, or metal with a high Z number. Examples of suitable metals include, but are not limited to: gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium, or a combination thereof.

According to some embodiments, said particle is a gold (Au) nanoparticle (GNP). A "gold nanoparticle" as used herein refers to a particle of gold (Au) having a particle size on the nanometer (nm) scale, generally less than 1 micrometer.

According to some embodiments, said GNP is a PEGylated GNP. According to some embodiments, said GNP is coated by a PEG layer. According to some embodiments, PEGylated coated GNPs prolongs the nanoparticles' blood circulation time and protects nanoparticles from detection by the immune system.

As used herein, the term "PEG" includes derivatives of PEG. As used herein "PEG or derivatives thereof" refers to any compound including at least one polyethylene glycol moiety. PEG polymers exist in linear forms, branched forms and/or multi-arm polyethylene glycols. In some embodiments, a PEG derivative includes PEG which is modified by the addition of one or more straight chain or branched C1-C6 alkyl groups. A PEG may further comprise a functional group. PEG molecules may be mono-, di-, or multifunctional polyethylene glycols. Non-limiting examples of functional groups include: a hydroxyl, a carboxyl, an amino, a phosphate, a phosphonate, a sulfate, asulfite, a sulfenate, a sulfonate, a sulfoxide, a sulfone, an amide, an ester, a ketone, an aldehyde, a nitrile, an alkene, an alkyne, an ether, a thiol (or mercapto), a hydroxyamic acid, a silane, a silicate, a carbamodithionate, a dithionate, a mercaptan, a disulfide, a peroxide and a nitronate group. In some embodiments, a PEG derivative comprises one or more groups selected from the group consisting of: acid (carbonic acid, sulphonic acid), aldehyde, COOH (carboxyl group), CHO, OCH$_3$ (methoxyl), CN, OH (hydroxyl group), OR, SH (thiol group/mercapto group), succinimidyl ester (NHS), SR, N3, NH2 (amine group) or NHR, wherein R=C1 to C4 chain.

According to some embodiments, the PEG layer comprises a mixture of thiol-polyethylene-glycol (mPEG-SH) (MW ~5 kDa) and a heterofunctional thiol-PEG-acid (SH-PEG-COOH) (MW ~5 kDa).

In some embodiments, the weight ratio of mPEG-SH to SH-PEG-COOH is in the range of 10:1 to 1:10. In some embodiments, the weight ratio of mPEG-SH to SH-PEG-COOH is in the range of 1:1 to 1:10. In some embodiments, the weight ratio of mPEG-SH to SH-PEG-COOH is in the range of 1:1 to 1:5. In some embodiments, the weight ratio of mPEG-SH to SH-PEG-COOH is in the range of 1:1 to 1:2. In some embodiments, the weight ratio of mPEG-SH to SH-PEG-COOH is about 2:3.

According to some embodiments, the peptide of the invention is directly attached (linked) to said particle (e.g., GNP). According to some embodiments, the peptide of the invention is linked to a PEGylated coated particle (e.g., GNP) via a functional group of said PEG. In some embodiments, said linkage is by a covalent bond.

In some embodiments, said peptide is chemically linked to said particle (e.g., GNP). As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

As used herein, the term "covalent attachment", "covalently attached", "covalently linked" and "covalently bonded" refer to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers attached covalently to a surface can also be bonded via means in addition to covalent attachment.

As used herein, the term "semi-covalent attachment" and "dative covalent bond" refers to a co-ordinate bond wherein the shared pair of electrons which form the bond come from the same atom. In the present disclosure, the dative covalent bond may occur between the metal, e.g. gold, and sulfur group.

Pharmaceutical Compositions

In another embodiment, there is provided a composition comprising the isolated peptide of the present invention and a pharmaceutical acceptable carrier.

The term "carrier" refers to a diluent, adjuvant, excipient, or vehicle with which the compound (e.g. the peptide or peptide conjugate described herein) is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Saline solutions and aqueous dextrose and glycerol solutions can also be employed as liquid carriers. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates.

The pharmaceutical compositions of the invention can be formulated in the form of a pharmaceutically acceptable salt of the peptides of the present invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the peptide of the invention, preferably in a substantially purified form, together with a suitable amount of carrier so as to provide the form for proper administration to the subject.

An embodiment of the invention relates to a peptide presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, the peptides of the present invention can be supplied in any manner suitable for the provision of the peptide to cells within the tissue of interest. Thus, for example, a composition containing the peptides of the present invention can be introduced, for example, into the systemic circulation, which will distribute said peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In an embodiment of the invention, peptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions of the present invention are generally administered in the form of a pharmaceutical composition comprising at least one of the active components of this invention together with a pharmaceutically acceptable carrier or diluent. Thus, the compositions of this invention can be administered either individually or together in any conventional oral, parenteral or transdermal dosage form.

Pharmaceutical compositions according to embodiments of the invention may contain 0.1%-95% of the active components(s) of this invention, preferably 1%-70%. In any event, the composition or formulation to be administered may contain a quantity of active components according to embodiments of the invention in an amount effective to treat the condition or disease of the subject being treated.

The peptides of the present invention, derivatives, or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

Therapeutic Use

According to another aspect, the present invention provides a method for treating a delta-opioid receptor (DOR) mediated disorder in a subject, the method comprising administering to the subject a pharmaceutical composition described herein (e.g., comprising the peptide of SEQ ID NO: 1 or 2) in an amount sufficient to ameliorate the disorder.

According to another aspect, the present invention provides a method of treating or ameliorating a medical condition amenable to treatment with an opioid receptor agonist, the method comprising administering to a subject in need thereof the pharmaceutical composition of the present invention, thereby treating said medical condition in said subject. According to some embodiments, said opioid receptor agonist is a delta opioid receptor agonist.

According to some embodiments, said medical condition is a substance abuse addiction. According to some embodiments, said substance is cocaine or a derivative thereof.

Additionally, the invention provides a method of treating pain in a subject, the method comprising administering to the subject a composition comprising the inventive compound in an amount sufficient to induce analgesia.

Efficacy in treating (i.e., reducing, easing, suppressing, or alleviating) pain in a subject in need thereof is determined using any suitable method. Analgesic efficacy is measured, for example, using a nociception assay in animals such as a tail withdrawal test, pain relief score, or a pain intensity difference score, optionally recorded at a given time point, or over time, or as compared to a baseline, and includes calculations based on area under the curve such as those plotting Total Pain Relief Score (TOTPAR) or the Sum of Pain Intensity Difference (SPID), as described in the Handbook of Pain Assessment, 2d. Turk & Meldzack, Eds., The Guilford Press, New York, N.Y. (2001). Increases in time to re-medication and increases in quality of life measurements also are indicators of successful pain treatment.

The term "pain" is used herein to represent all categories of physical pain. This includes traumatic pain resulting from injury, surgery or inflammation as well as pain associated with diseases such as cancer, AIDS, arthritis, and herpes. Pain can be associated with neuropathy such as diabetic neuropathy, causalgia, brachial plexus avulsion, occipital neuralgia, fibromyalgia, vulvodynia, prostadynia, pelvic pain, gout, and other forms of neuralgia, such as neuropathic and idiopathic pain syndromes. Specific organ- or site-localized pain, such as headache, ocular and corneal pain, bone pain, urogenital pain, heart pain, skin/burn pain, lung pain, visceral (kidney, gall bladder, etc.) pain, joint pain, dental pain and muscle pain are included in this invention. The general term "pain" also covers pain symptoms of varying severity, i.e. mild, moderate and severe pain, as well as those of acute and chronic pain.

Non-limiting examples of pain includes inflammatory pain selected from the group consisting of organ transplant rejection; reoxygenation injury resulting from organ transplantation, chronic inflammatory diseases of the joints, arthritis, rheumatoid arthritis, osteoarthritis, bone diseases associated with increased bone resorption, inflammatory lung diseases, asthma, adult respiratory distress syndrome, chronic obstructive airway disease, inflammatory diseases of the eye, corneal dystrophy, trachoma, onchocerciasis, uveitis, sympathetic ophthalmitisendophthalmitis, chronic inflammatory diseases of the gum, gingivitis, periodontitis, tuberculosis, leprosy, inflammatory diseases of the kidney, uremic complications, glomerulonephritis, nephrosis, inflammatory diseases of the skin, sclerodermatitis, psoriasis and eczema, inflammatory diseases of the central nervous system, chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis, viral or autoimmune encephalitis, autoimmune diseases, Type I and Type II diabetes mellitus, diabetic complications, diabetic cataract, glaucoma, retinopathy, nephropathy, microaluminuria, progressive diabetic nephropathy, polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, skin or mucous membrane complication, immune-complex vasculitis, systemic lupus erythematosus (SLE), inflammatory diseases of the heart, cardiomyopathy, ischemic heartdisease hypercholesterolemia, atherosclerosis, preeclampsia, chronic liver failure, brain and spinal cord trauma, and inflammatory associated cancer.

In embodiments the pain to be treated can be, for example, a peripheral neuropathy, a central neuropathy, a traumatic abnormality, a cerebral vascular accident, postoperative pain, dental pain, direct trauma, infection, HIV infection, small pox infection, herpes infection, toxic exposure, exposure to arsenic, exposure to lead, cancer, invasive cancer, congenital defect, phantom limb pain, encephalitis, rheumatoid arthritis, fibromyalgias, spinal root lesions, spinal root impingement, back pain, multiple sclerosis, chronic pain, fibrous tissue pain, muscle pain, tendon pain, ligament pain, pain associated with diarrhea, irritable bowel syndrome, abdominal pain, chronic fatigue syndrome, and spasms.

According to another embodiment, the pharmaceutical composition is used for the treatment, prevention and/or reversal of neuropathic pain and inflammatory nociceptive pain, such as inflammatory arthritic pain, rheumatoid arthritis, back pain, chronic pain, diabetic neuropathic pain, trigeminal neuralgia pain, phantom limb pain, complex regional pain syndrome pain, acute herpetic pain, post herpetic pain, causalgia pain, idiopathic pain, inflammatory pain, cancer pain, postoperative pain, fibromyalgia pain, headache pain, migraine pain, allodynia pain, vulvodynia pain, interstitial cystitis pain, irritable bowel syndrome (IBS), arthritic joint pain and tendinitis.

By "treating" is meant the medical management of a patient with the intent that a cure, amelioration, or prevention of a dependency or a relapse or associated disease, pathological condition, or disorder will result. This term includes active treatment, that is, treatment directed specifically toward improvement of the dependency or associated cure of a disease, pathological condition, or disorder, and also includes causal treatment, that is, treatment directed toward removal of the cause of the dependency or associated disease, pathological condition, or disorder. In addition, this term includes palliative treatment, that is, treatment designed for the relief of symptoms rather than the curing of the dependency, disease, pathological condition, or disorder; preventive treatment, that is, treatment directed to prevention of the dependency or associated disease, pathological condition, or disorder; and supportive treatment, that is, treatment employed to supplement another specific therapy directed toward the improvement of the dependency or associated disease, pathological condition, or disorder. The term "treating" also includes symptomatic treatment, that is, treatment directed toward constitutional symptoms of the dependency or an associated disease, pathological condition, or disorder. By "stimulant" is meant any substance that temporarily increases functional activity, and preferably cardiac, respiratory, cerebral, nervous, vascular, motor, or vasomotor functional activity. Preferred stimulants include, without limitation, cocaine craving for a drug that may or may not be accompanied by a physiological dependency, as well as a state in which there is a compulsion to take a drug, either continuously or periodically, in order to experience its psychic effects or to avoid the discomfort of its absence. Forms of "dependency" include habituation, that is, an emotional or psychological dependence on a compound to obtain relief from tension and emotional discomfort, as well as physical or physiological dependence, that is, use of a compound to prevent withdrawal symptoms.

"Treating" pain or an opioid receptor-associated disorder does not require a 100% abolition of pain or the disorder. Any decrease in pain sensation or symptoms of the disorder constitutes a beneficial biological effect in a subject. In this regard, the invention reduces pain or the symptoms of an opioid receptor-associated disorder by, e.g., at least about 5%, at least about 10% or at least about 20% compared to levels of, e.g., pain observed in the absence of the inventive method (e.g., in a biologically-matched control subject, subject that is not administered the inventive compound, or the subject administered the compound prior to treatment).

In some embodiments, pain is reduced by at least about 30%, at least about 40%, at least about 50%, or at least about 60%. In some embodiments, the inventive method inhibits pain by at least about 70%, at least about 80%, at least about 90%, or more (about 100%) compared to that experienced in the absence of the inventive method.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the invention should be sufficient to affect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

A "therapeutically effective amount" of the peptide is that amount of peptide which is sufficient to provide a beneficial effect to the subject to which the peptide is administered. More specifically, a therapeutically effective amount means an amount of the peptide effective to prevent, alleviate or ameliorate tissue damage or symptoms of a disease of the subject being treated.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods:

Cells.

NG108-15 rat hybridoma cells were grown at 37° C. in DMEM supplemented with 10% FBS, HAT supplement, 1.5 g/l sodium bicarbonate, 2 mM glutamine, antibiotics and 5% $CO_2$. Rat C6 glioma cells, mouse 3T3 fibroblasts, human PC-3 prostate carcinoma cells, human MDA-MB-435 breast carcinoma cells, human CHRF megakaryoblastic cells and MPB mouse hybridoma cells were grown in similar medium without HAT.

Surface Opioid Receptor Expression.

Cells at 70% confluence were scraped from the culture disk, centrifuged at 1500 rpm, 4° C. for 5 min and the cell pellet was re-suspended in PBS/0.05% FBS to a concentration of $10^7$/ml. Two microliters of polyclonal rabbit IgG anti-μ-opioid receptor (Sigma-Aldrich, Israel) or rabbit IgG anti-δ-opioid receptor (Abcam, Zotal, Jerusalem) was added to 100 μl of cell suspension for 60 min on ice and then centrifuged for 5 min at 4250 rpm, 4° C. The cell pellet was re-suspended in 500 μl of PBS/0.05% FBS and 1 μl of goat anti-rabbit IgG-FITC conjugate. The mixture was incubated for 30 min on ice and re-centrifuged. The cell pellet was re-suspended in 400 μl of PBS and fluorescent staining was measured by flow cytometry on a FACS Calibur (Beckman-Dickinson).

Negative Selection of Non-Specific Phage Clones.

In order to remove from the phage pool clones which display peptides recognizing non-relevant targets, the 12mer phage display peptide pool (Ph.D-12, New England Biolabs Inc, Ipswich, Mass., USA) was sequentially absorbed on a series of cells not expressing the target receptor. The order of cells was PC-3, CHRF, MDA-MB-435, MBP, 3T3. So each cell type $10^4$ cells were plated in a microplate well (Greiner) and the cells were growth overnight to 70-80% confluence. The cells were washed carefully thrice with PBS and then 300 μl blocking buffer (PBS/0.1% BSA) was added for 1 hr at 4° C. The wells were then carefully washed 6 times with PBS. A mixture of 10 μl phage pool ($2 \times 10^{11}$ phage) and 100 μl PBS was added to the first cell type and the well incubated at room temperature for one hour with gentle rotation. The supernatant containing the non-absorbed phage was carefully collected and added to the well containing the next cell type. After absorption on 3T3 cells, the collected supernatant, referred to as the "absorbed phage pool" was collected and stored at −200 C, except for 3 μl which were used for titration, performed as described by the manufacturer.

Positive Selection of δ Opioid Receptor-Specific Phage Clones.

Figure 3A:
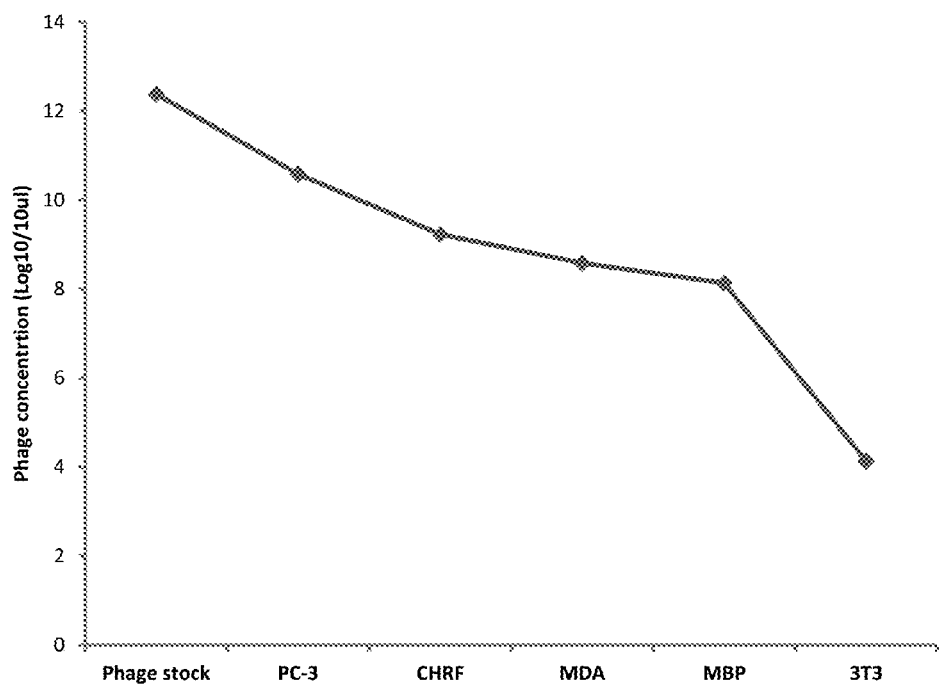
FIGS. 3A-E. Inhibition of phage clone binding to C6 cells by the δ-, or μ-opioid agonist DSLET (CAS Reg. No. 75644-90-5) or DAMGO (CAS Reg. No. 78123-71-4), respectively.
Figure 3B:
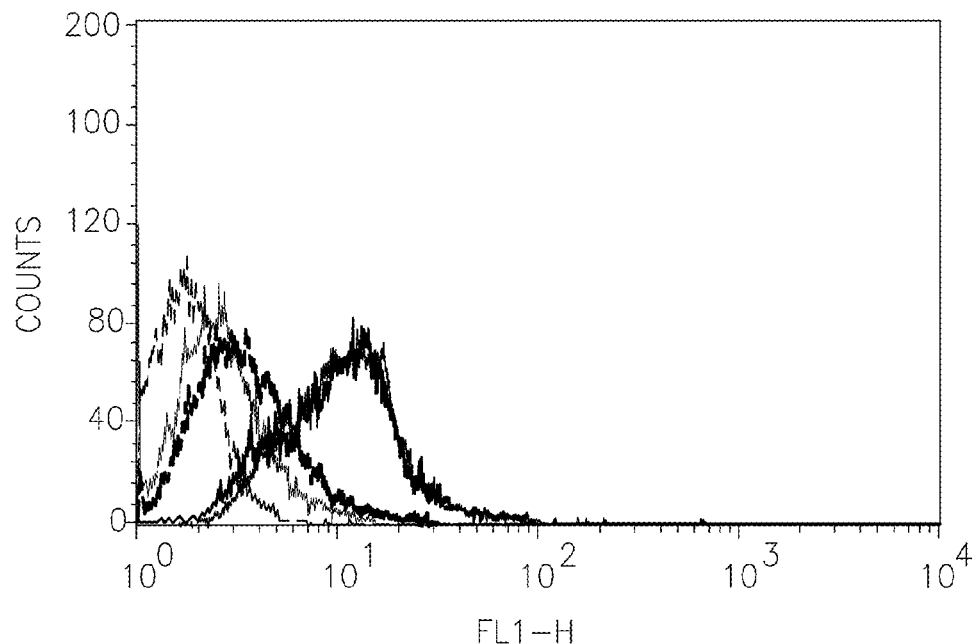
Figure 3B:
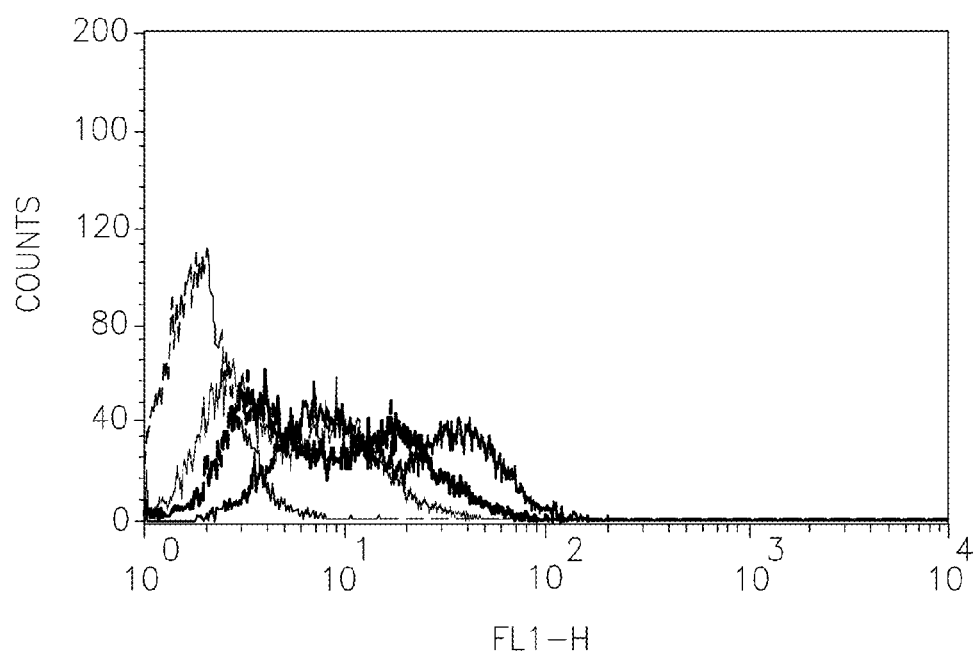
Figure 3C:
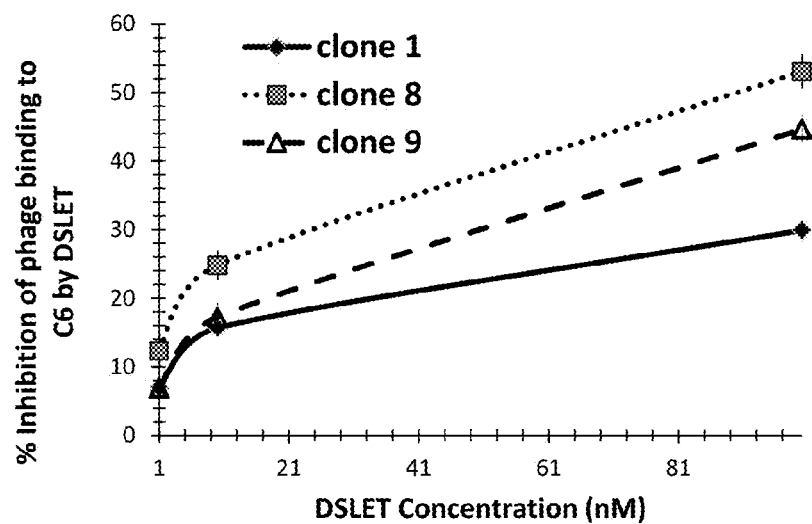
Figure 3D:
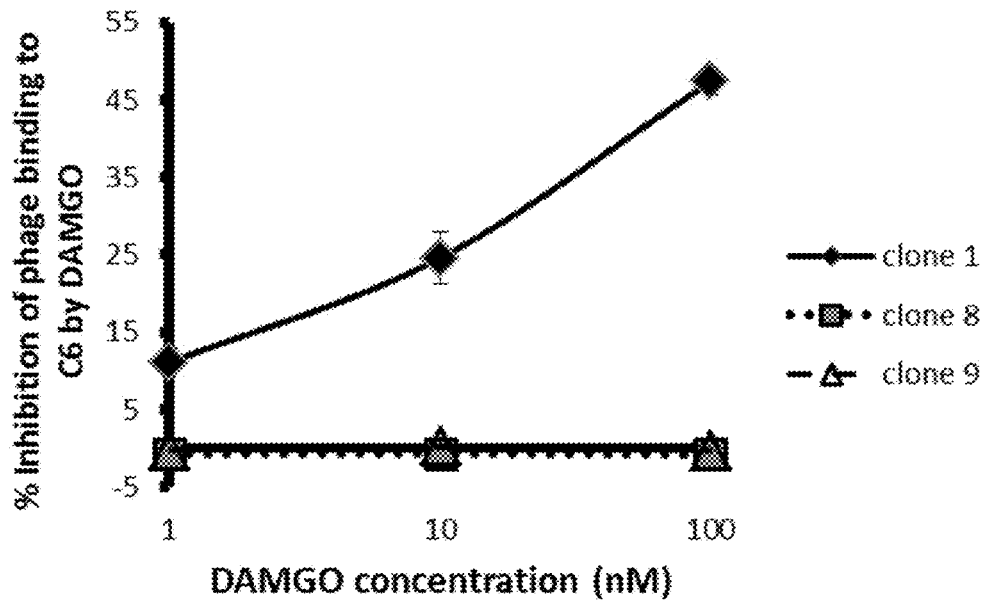

C6 glioma cells were cultured as described above. Flow Cytometry analysis showed that 90% of the cells expressed the δ-opioid receptor and 50% expressed the μ-opioid receptor (FIG. 3D). A mixture of 10 μl pre-absorbed phage ($2 \times 10^{11}$ phage) and 100 μl PBS was added to the cells and the microplate incubated at room temperature for one hour with gentle rotation after which the supernatant containing the non-absorbed phage was carefully removed. The cells were washed thrice with PBS and then 100 μl of elution buffer (1 mg/ml BSA/0.2M Glycine-HCl, pH. 2.2) was added. After gentle rotation of the microplate for 10 min at room temperature, 15 μl of 1M Tris-HCl (pH 9.1) was added to neutralize the solution. The supernatant was collected and the recovered phage were collected and stored except for 3 μl which was titrated on E. coli lawns. From the phage dilution that produced 100-200 plaques, 15 phage colonies were randomly chosen. These clones were amplified, their DNA isolated and the peptide inserts were sequenced.

Phage ELISA Binding Assay.

To calibrate the binding of peptide-displaying phage to the target cells, C6 cells were cultured as described above, washed three times with PBS, fixed with 4% formaldehyde for 15 min at room temperature and washed again. $Log_{10}$ serial dilutions of candidate δ-opioid receptor binding phage clones, and a non-peptide displaying control M13 phage clone (M13KE, New England Biolabs) were prepared in PBS 1 mg/ml BSA) and incubated with the cells for 1 hr at room temperature. The cells were washed and 100 μl of monoclonal anti-M13 antibody-HRP conjugate (GE Healthcare, Pittsburgh, USA) was added to the wells for 30 min at room temperature. After washing, 200 μl TMB/E solution was added for 5 min in the dark at room temperature. Then 15 μl 2M $H_2SO_4$ was added. Optical density in the wells was measured at 450 nm using a TECAN Infinite M200 spectrophotometer.

To validate the δ-receptor binding capability of the C6 binding clones in a competitive assay, C6 cells were prepared as described above. A mixture of $10^8$ phage particles (this value was in the center of the linear portion of the phage binding calibration curves from above) and 0, 1, 10 or 100 nM of either the δ-opioid receptor agonist DSLET or the μ-opioid receptor agonist DAMGO and then added to the fixed cells for 1 hr at room temperature. The cells were washed ×3 with PBS and the presence of phage enumerated as described above.

Validation of Peptide Specificity for δ-Opioid Receptor Binding.

DNA was isolated from phage clones demonstrating positive competitive binding versus the DSLET analogue and negative competition versus the DMGO analogue (according to the manufacturer's instructions) and the peptide insert sequenced. The derived peptides were synthesized (Pepmic, Suzhou, China). The binding specificity of the peptides was tested in a competitive assay. C6 cells were grown to 70-80% confluence and removed from the culture, centrifuged and re-suspended to 2×10⁶/ml in PBS/0.05% FBS. D-SLET-FITC (3.5 nM) was mixture with 0, 3.5, 10, 50 or 100 nM of peptide. In parallel, 2 nM DAMGO-FITC was mixture with 0, 2, 10, 50 or 100 nM of peptide. These mixtures (500 µl) were added to the cells for 5 min at 37° C. Then 500 µl PBS was added and the tubes centrifuge for 5 min at 4250 rpm. The cell pellet was re-suspended in PBS and analyzed by flow cytometry.

Pharmacological Function of the Peptides.

To test the pharmacological function of the peptides showing positive competitive binding versus the DSLET analogue and negative competition versus the DMGO analogue were tested for agonistic activity using the Direct cAMP kit (Enzo). The analogue DSLET was used as a positive control.

Gold Nanoparticles' Synthesis, Conjugation and Characterization.

Synthesis.

Synthesis of 20 nm spherical GNPs was carried out using sodium citrate as a reducing agent (e.g., under Entüstün & Turkevic's methodology). 414 µL of 50% w/V HAuCl4 solution were added to 200 mL purified water, and the solution was heated in an oil bath on a heating plate until boiling. Then, 4.04 mL of 10% sodium citrate solution were added, and the solution was stirred for 10 min. After cooling to room temperature, the solution was centrifuged until precipitation of the nanoparticles.

Conjugation.

GNPs were coated with a PEG layer, in order to prolong nanoparticles' blood circulation time and to protect nanoparticles from detection by the immune system. The PEG layer consists of a mixture of thiol-polyethylene-glycol (mPEG-SH) (~40%, MW ~5 kDa) and a heterofunctional thiol-PEG-acid (SH-PEG-COOH) (~60%, MW ~5 kDa). The PEG mixture was added in excess and the solution was stirred for 4 h at room temperature. Following this step, the solution was centrifuged in order to remove excess PEG molecules and reach higher concentrations. The peptide, which specifically targets the DOR receptor, was then covalently conjugated to the carboxylic group of the SH-PEG-COOH, after activation with EDC (1-ethyl-3-(3-dimethylaminopropyl) carbodiimide HCl, ThermoScientific) and NHS (N-hydroxysulfosuccinimide sodium salt, Chem-Impex International), by adding all three to the PEG-GNP solution and stirring the mixture overnight. Centrifugation was performed until a final Au concentration of 30 mg mL-1 was reached.

Characterization.

The GNP-peptidel were characterized using dynamic light scattering (DLS; Malvern Instruments, Malvern, UK), ultraviolet-visible spectroscopy (UV-Vis; UV-1650 PC; Shimadzu Corporation, Kyoto Japan), and zeta potential (Zeta-Sizer 3000HS; Malvern Instruments, Malvern, UK), following each level of coating.

In Vitro Cell Binding Study.

C6 cells (1×10⁶) were cultured in 5 ml glucose-free DMEM medium containing 5% FCS, 0.5% Penicillin and 0.5% Glutamine. Then, excess amounts of GNPs were added and incubated with cells for 30 minutes at 37° C.

Confocal Microscopy Experiment.

Fluorescent coated (Rhodamine B, Sigma, Israel) GNP-peptidl were incubated with C6 cells for 30 min at 37° C. The cells were subsequently washed three times in PBS prior to confocal imaging using Leica TCS SP5 with Acousto-Optical Beam Splitter microscope to acquire fluorescent and bright field images.

Dark-Field Microscopy.

A Nikon i50 microscope (Tokyo, Japan) equipped with a hyperspectral imaging system (CRI, USA) was used to obtain dark-field images (20× magnification) in order to assess nanoparticle uptake.

Fluorescence-activated cell sorter (FACS) analysis of Surface opioid receptor expression. Cells at 70% confluence were scraped from the culture disk, centrifuged at 1500 rpm, 40 C for 5 min and the cell pellet was re-suspended in PBS/0.05% FBS to a concentration of 107/ml. Two microliters of polyclonal rabbit IgG anti-µ-opioid receptor (Sigma-Aldrich, Israel) or rabbit IgG anti-δ-opioid receptor (Abcam) was added to 100 µl of cell suspension for 60 min on ice and then centrifuged for 5 min at 4250 rpm, 40 C. The cell pellet was re-suspended in 500 µl of PBS/0.05% FBS and 1 µl of goat anti-rabbit IgG-FITC conjugate. The mixture was incubated for 30 min on ice and re-centrifuged. The cell pellet was re-suspended in 400 µl of PBS and fluorescent staining was measured by flow cytometry on a FACS Calibur (Beckman-Dickinson).

Fluorescence-Activated Cell Sorter (FACS) Analysis of Nanoparticle Cellular Uptake.

Cells were incubated with GNP-peptide for 15 min at 37° C. and then washed with PBS, followed by trypsin treatment. Then, cells were centrifuged twice (5 min in 1000 rpm) to wash out unbound nanoparticles. Cells were analyzed for cell-associated NPs by Flow Cytometry (FACS; Cellquest software; Becton-Dickinson & Co., Franklin Lakes, N.J.).

Animals.

Male Sprague-Dawley rats (Harlan, Israel) weighing 250-350 g were maintained on a 12-hr light/12-hr dark reversed cycle, with food and water available ad libitum. Rats were housed 2 per cage with a metal perforated divider between them. Experiments were conducted during the dark cycle. All experimental procedures were approved by the University Animal Care and Use Committees and were performed in accordance with National Institutes of Health guidelines.

Guided Cannula Implantation.

Rats were anesthetized with xylazine and ketamine (10 mg/kg and 100 mg/kg, respectively). A 20-gauge guide cannula was then unilaterally implanted either into the NAc (AP, +1.4 mm; LM, +1.2 mm to bregma and DV, −5.6 mm) or dorsal striatum (AP +1.4 mm; LM +2.4 mm to bregma and DV, −4.4) of rats with the aid of a stereotactic device (David-Kopf Instruments, CA., USA).

Jugular Vein Catheterization.

Immediately after cannula implantation, rats were implanted with intravenous silastic catheters (ID 0.55 mm, OD 0.94 mm, Dow Corning, Mich.) into the right jugular vein. The catheter was secured to the vein with silk sutures and was passed subcutaneously to the top of the skull, where it exited into a connector (a modified 22-gauge cannula; Plastics One, VA, USA) mounted to the skull with MX-80 screws (Small Parts, Inc., FL, USA) and dental cement (Yates and Bird, IL, USA).

Self-Administration Training Sessions.

The self-administration chambers (Med-Associates, Inc.; St Albans, Vt., USA) had two levers, one active and one inactive. An active lever press generated a cocaine infusion (0.75 mg/kg, 0.13 ml, 5 sec/infusion; cocaine obtained from the National Institutes on Drug Abuse, MD, USA) through the i.v. catheter, and also activated a light located above the lever, which was lit for 40 sec. Active lever presses during the last 35 sec of the light cue did not result in additional cocaine infusion. Presses on the inactive lever did not activate the infusion pump and light. The number of active lever responses, infusions, and inactive lever responses were recorded. Rats were returned to their home cages at the end of the daily session.

Forced Abstinence.

Immediately after the 10-day period of self-administration training sessions, rats were subjected to either a 1-day or a 30-day period of forced abstinence. During abstinence, rats were left in their home cages and handled 3 times a week.

Cue-Induced Cocaine-Seeking Behavioral Test.

On day 1 or day 30 of forced abstinence, rats were again placed in the self-administration chambers, connected to the infusion line, and drug-seeking behavior was tested for 60 min. Upon active lever presses, only the contingent light cue appeared, without delivery of either saline or cocaine.

Drugs and Intracranial Infusions.

The two novel peptides (1000 ng and 5000 ng each) were dissolved in a CSF. The peptides were infused (5 min, 0.2 ul/min) into the NAc via the guide cannula, using an electronical syringe pump (CMA 400, CMA/Microdialysis). Control rats received similar infusions of a CSF only (5 min, 0.2 ul/min) into the same brain region as treated rats. Infusions were performed immediately (<5 min) before testing of cue-induced cocaine-seeking behavior. The internal cannula remained in place for 5 min after infusion, to avoid reflux.

Example 1

Negative Selection of Non-Relevant Phage Clones

The phage stock pool was incubated sequentially on a series of off-target cells representing fibroblasts, lymphocytes and several tissues, in order to remove as many phage clones as possible that bound irrelevant cell membrane components. FIG. 3A shows the decrease in $log_{10}$ concentration after incubation on each cell type. At the end of the process, the phage concentration had been reduced by almost 8 orders of magnitude. This "absorbed phage pool" was used for positive selection of target-binding phage.

Example 2

Figure 3E:
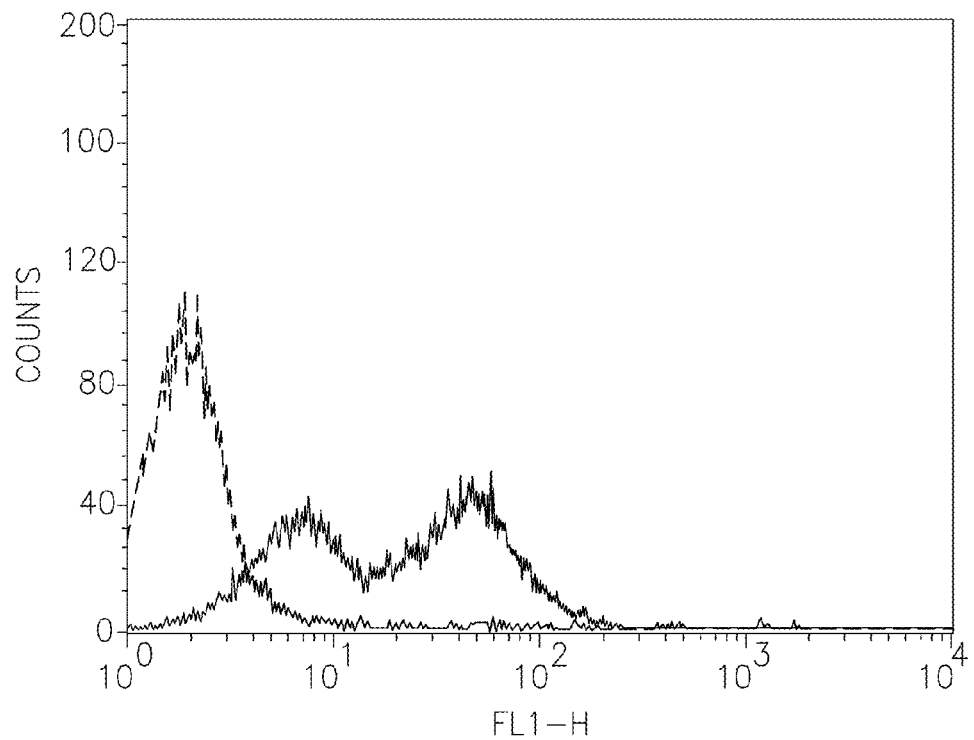
Figure 3E:
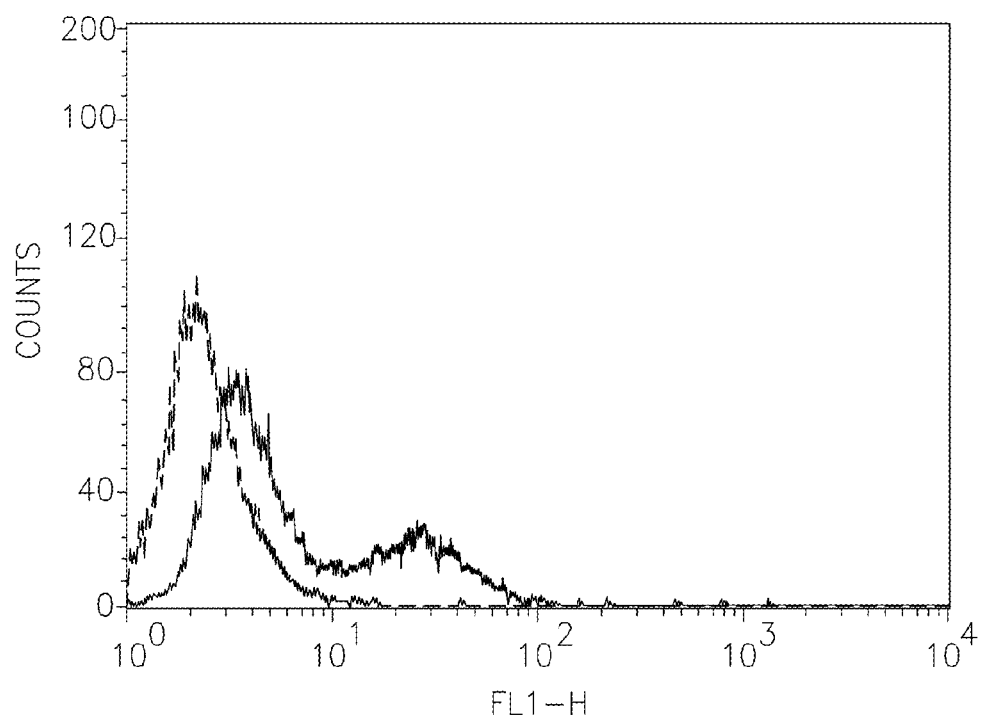

Positive Selection of δ-Opioid Binding Phage Clones and their Displayed Peptide Sequences C6 glioma cells were used to positively select δ-opioid binding phage. Flow cytometry assays showed that 90% of the cells expressed the δ-form of the receptor and 50% expressed the μ-form (FIG. 3E). C6 cells were exposed to the absorbed phage pool, washed and bound phage eluted. After titration, 15 individual clones were randomly selected, amplified and the DNA and amino acid sequences of their displayed peptides determined.

Table 1 shows their amino acid sequences. While in almost every position there was repetition of amino acids between the clones, preliminary analysis did not reveal a consensus sequences between the clones.

TABLE 1

| Peptide | Position in peptide | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 1 | Asp | Pro | Gln | Val | Thr | Gly | Arg | His | Trp | His | Asp | Leu |
| 2 | Ala | Tyr | Glu | Gly | Pro | Gln | Ile | Ile | Ala | Ser | Lys | Ser |
| 3 | Lys | Gly | Pro | Thr | Thr | Ser | Glu | Leu | Asn | Ser | Pro | Lys |
| 4 | Thr | Asp | Leu | Lys | Ser | Ser | Tyr | Ser | Pro | Arg | Trp | Leu |
| 5 | Asp | Asp | Leu | Arg | Asp | Ser | Met | Arg | Ser | Ala | Ala | Pro |
| 6 | Phe | Tyr | Ser | Glu | Ser | Asn | Leu | Trp | Leu | Glu | Glu | Met |
| 7 | Asn | Pro | Phe | Met | Leu | Lys | Phe | Pro | Pro | Glu | Asn | Thr |
| 8 | Ile | Ile | Ala | Gly | Glu | Tyr | Lys | Gln | Met | Leu | Thr | Leu |
| 9 | Asn | Gly | Asn | Asp | Arg | Thr | Asp | Gln | Met | Pro | Leu | Pro |
| 10 | Phe | Thr | Leu | Pro | Lys | Ser | Pro | Ser | Pro | Gly- | Phe | Leu |
| 11 | Phe | Gln | Gly | Gly | Ser | Tyr | Asn | Ala | Ser | Gln | Ile | Pro |
| 12* | Asn | Val | Glu | Ser | Ile | Ser | Ala | Asn | Tyr | Lys | Met | Tyr |
| 13 | Ser | Ala | Trp | Arg | Asp | Ser | Ala | Gln | Thr | Gln | Thr | Leu |
| 14 | Ser | Ile | Glu | Pro | Trp | Trp | Gly | Leu | Pro | Val | Lys | Gly |
| 15 | Glu | Asp | Met | Asn | Gly | Ser | Ser | Arg | Met | Gln | Ile | His |

Example 3

Validation of δ-Opioid Receptor Binding

Figure 1B:
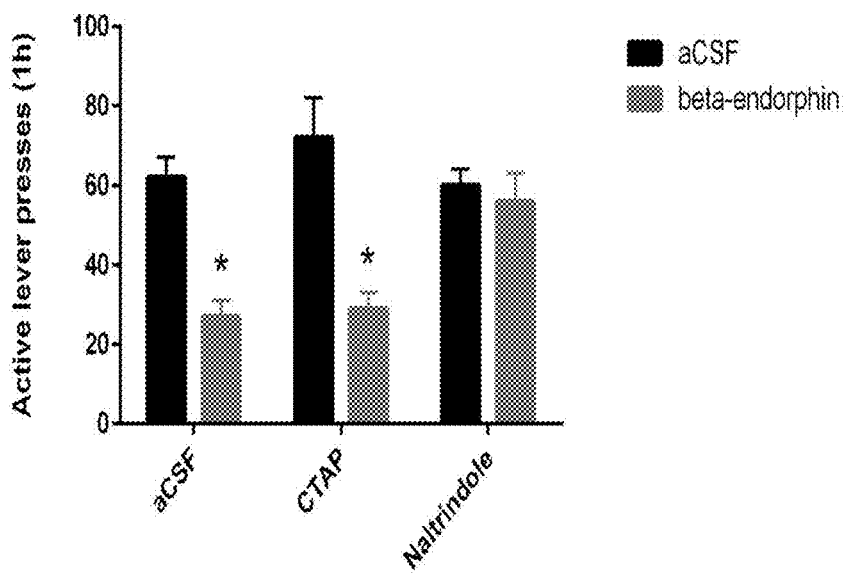
Figure 2:
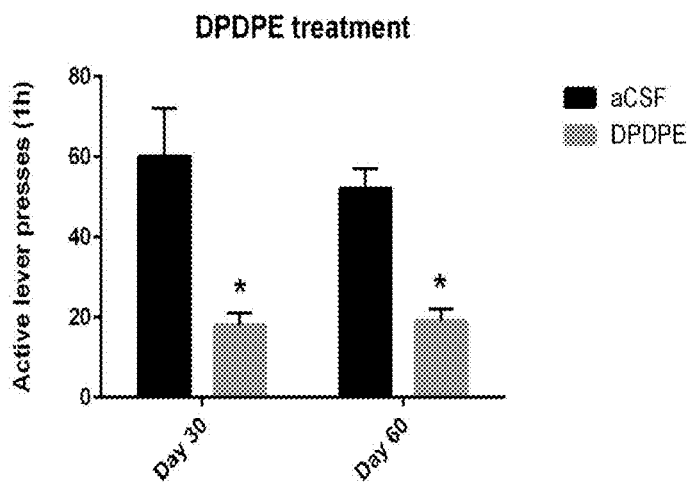
FIG. 2. A bar-graph showing active lever pressure of a commercial pure delta agonist ("DPDPE"), injected into the NAc, compared to a CSF-injected group. DPDPE was injected once, after 30 days of abstinence. The reduced seeking behavior was observed both at days 30 and 60 of forced abstinence. N=6 per group.

The 15 C6-binding phage clones were tested for δ-opioid receptor binding in a competitive cell-ELISA versus the δ-receptor agonist DSLET. FIG. 1A shows that 3 clones, nos. 1, 8 and 9, inhibited significantly the binding of agonist at both 20 and 100 nM concentrations. The 12 other clones were unable to inhibit DSLET binding and presumably bind to other C6 membrane components. Clones 1, 8 and 9 were then tested for their ability to compete with the binding of the μ-opioid agonist DAMGO. The results, shown in FIG. 1B, reveal that the peptide displayed by clone 1 was also able to inhibit DAMGO binding, but those displayed by clones 8 and 9 were not. On the basis of these results, further studies were carried out on clones 8 and 9. The peptides displayed by these clones were synthesized. The peptide displayed by clone 9 was renamed Peptide 1 and that displayed by clone 8 was renamed Peptide 2.

To validate that the free peptides indeed bound specifically to the δ-receptor as did their parent clones, direct competitive assays were performed against DSLET-FITC or DAMGO-FITC. The optimal concentrations of labeled peptide for these assays were determined by calibrating the level of their binding the C6 by flow Cytometry (FIG. 3B). Sub-saturation concentrations selected were 3.5 nM for DSLET-FITC and 2 nM for DAMGO-FITC. Peptides 1 and 2 were then tested for δ-receptor binding. Another known δ-receptor agonist, DPDPE, was included as a positive control and an irrelevant 12-mer peptide, AP, as a negative control. FIG. 3C shows that Peptide 1 and 2 successfully competed with DSLET-FITC producing a maximum of 48% and 45% inhibition respectively at 100 nM. The negative peptide (AP) produced only background inhibition of 19% at this concentration. To validate δ-receptor specificity, similar experiments were performed using DAMGO-FITC and free DAMGO as the positive control. FIG. 3D shows that neither Peptide 1 or 2 inhibited binding to the μ-opioid receptor. These results confirmed the binding specificity of the peptides for the δ-opioid receptor.

Example 4

Pharmacological Functionality of Peptides 1 and 2

Figure 4A:
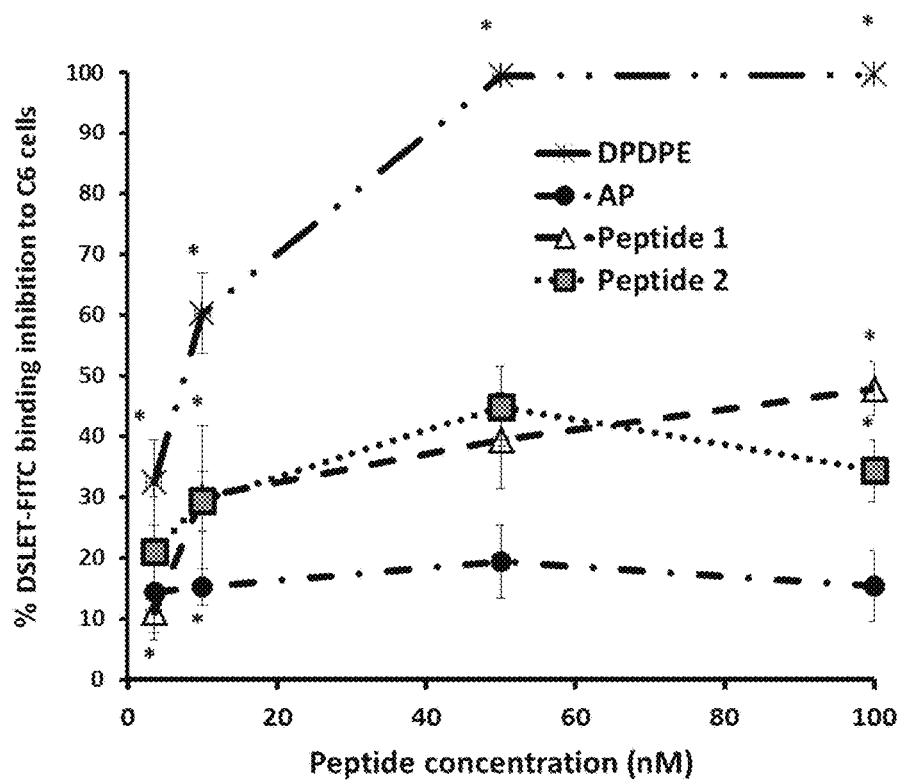
FIGS. 4A-B. Peptides 1 and 2 inhibit δ-opioid receptor agonist binding. (4A) DSLET-FITC (3.5 nM) was mixed with 0, 3.5, 10, 50 or 100 nM of peptide 1 or 2 and then added to C6 cells. Another known δ-receptor agonist, DPDPE, was used as a positive control and an irrelevant 12-mer peptide, AP, was used as a negative control. (4B) 2 nM DAMGO-FITC was mixed with 0, 2, 10, 50 or 100 nM of peptide 1 or 2 and then added to C6 cells. Free DAMGO was used as the positive control and AP was used as a negative control. After incubation and centrifugation, the cell pellet was re-suspended in PBS and analyzed by flow cytometry.
Figure 4B:
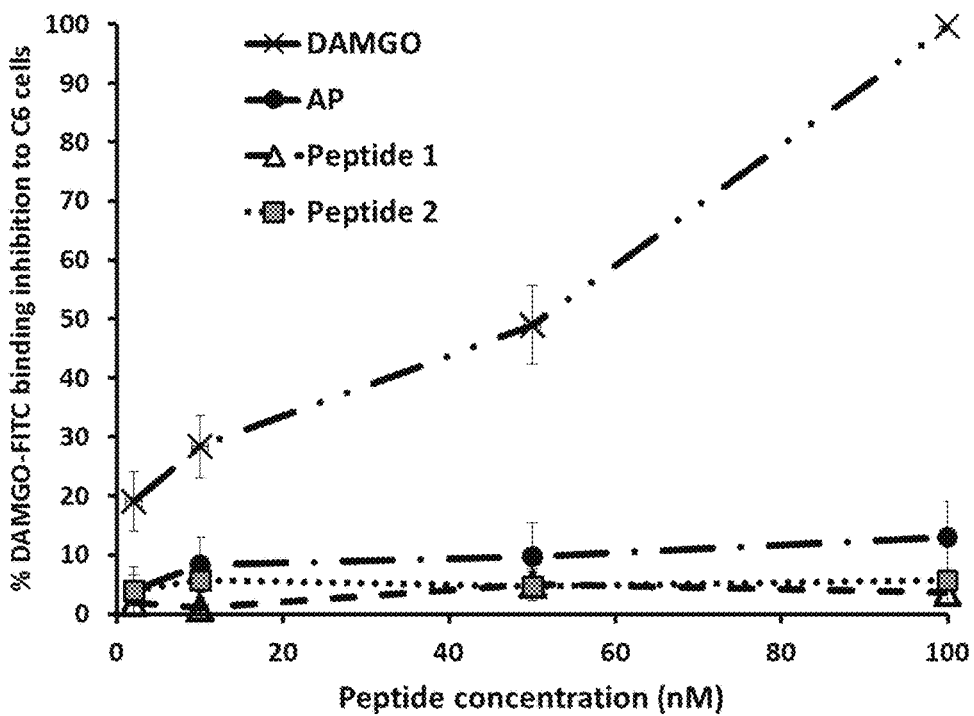
Figure 5:
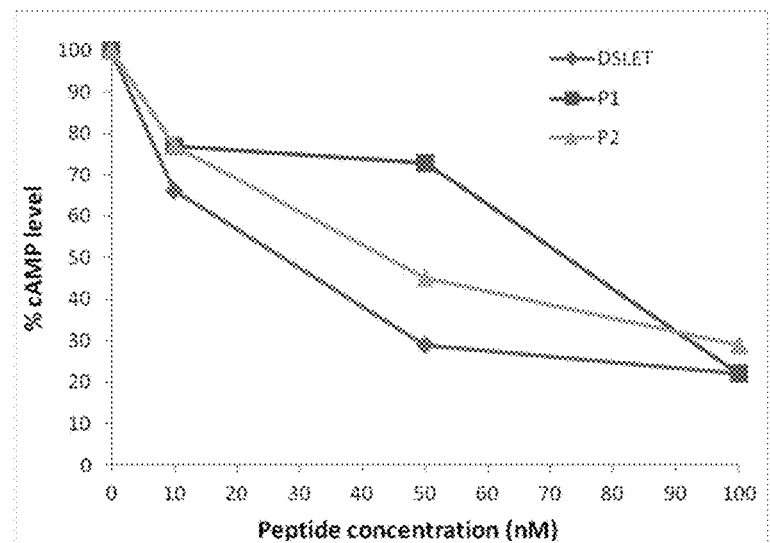
FIG. 5. Determination of pharmacological activity of peptides 1 (P1) and 2 (P2). A commercial kit was used to measure the level of intracellular cyclic AMP in C6 cells following exposure to increasing concentrations of peptide 1 or 2. DSLET was used as a positive control.
Figure 6:
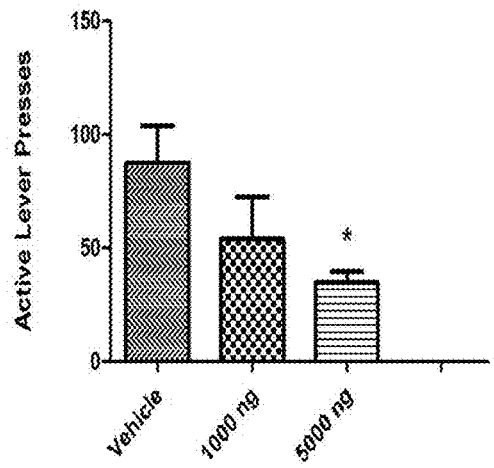
FIG. 6. A bar graph showing decreased active lever presses for peptide 1 compared to a CSF group, upon injection into the NAc. Results show the effect of two doses. n=7 per group.
Figure 7:
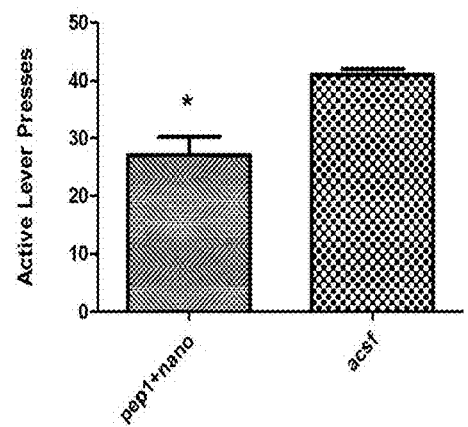
FIG. 7. A bar graph showing decreased active lever presses for peptide 1 conjugated to gold nanoparticles compared to a CSF group, upon injection into the NAc. n=5 per group.
Figure 8:
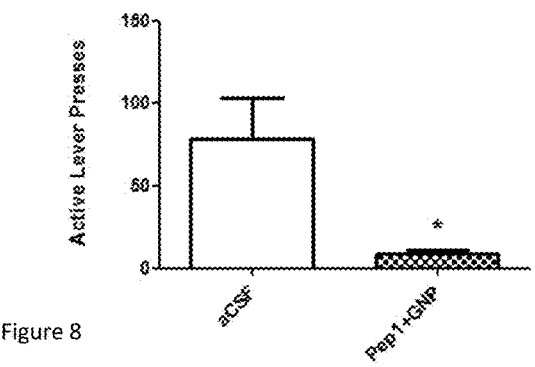
FIG. 8. A bar graph showing decreased active lever presses for peptide 1 conjugated to gold nanoparticles compared to a CSF group, upon intra-nasal injection. Significantly less active lever presses compared to a CSF group was observed. Rats were anesthetized for the intra-nasal procedure and two hours later they were placed in the self-administration chambers for drug seeking behavior test. N=4-5 per group.

The pharmacological activity of Peptides 1 and 2 was evaluated by testing their ability to influence the level of intracellular cyclic AMP in C6 cells. FIG. 4 clearly demonstrates that both peptides significantly reduced cAMP levels in a dose-dependent manner; at 100 nM, both peptides were as effective as the DSLET control agonists, reducing cAMP levels by almost 80%. These results indicate that both peptides function as δ-receptor agonists.

In this experiment, the peptides of the invention were infused into the NAc on day 30 of abstinence, and the response to cocaine cues was examined (n=6-8 per group). Student's t-test revealed a significant effect for the peptides in reducing cocaine seeking behavior, related to a CSF treated rats ($p<0.05$).

Example 5

Conjugation of the Peptide of the Invention to Gold Nanoparticles

The C6 cells that were cultivated in the lab were used in order to examine their MOR and DOR expression. The FACS display was analyzed by unpaired t-test and revealed significant higher expression of the DOR among the C6 cells relative to the MOR expression ($P<0.05$) (FIG. 9).

The C6 cells that were cultivated in the lab were used in order to examine the binding efficiency of the peptide to the DOR located on the C6 cells. The FACS display was analyzed by unpaired t-test and revealed significant higher affinity to the DOR among the C6 cells relative to the vehicle ($P<0.05$) (FIG. 10)

Figure 11A:
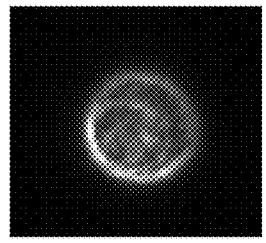
FIGS. 11A-C. Microscope validation of the binding. (11A) Gold nanoparticle (GNP) conjugated peptide 1 bind mainly the C6 cells membrane. (11B). Blocking the DOR using Naltrindole prevented the binding of the peptide to the cells membrane. (11C). Blocking the DOR using Naltrindole followed by adding glucose to GNP resulted in massive flow of GNP into the cells.
Figure 11B:
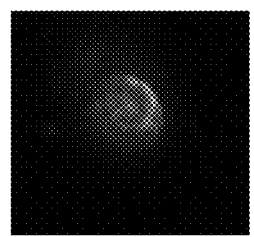
Figure 11C:
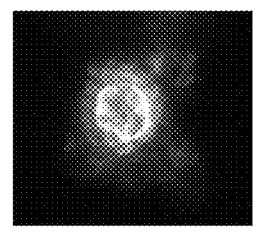

To further validate these findings, samples were placed in the microscope and binding to the cells membrane was examined. Peptide 1 conjugated to GNP showed higher affinity by demonstrating increased binding to the C6 cells membrane while blocking the DOR with Naltrindole resulted in a significant decrease in the binding. Adding Glucose to the GNP-Naltrindole complex caused massive flow of the GNP-Glucose but this flow was not specific as binding occurred through the entire cell and not only on the membrane as seen in FIG. 3A (FIG. 11).

Figure 12A:
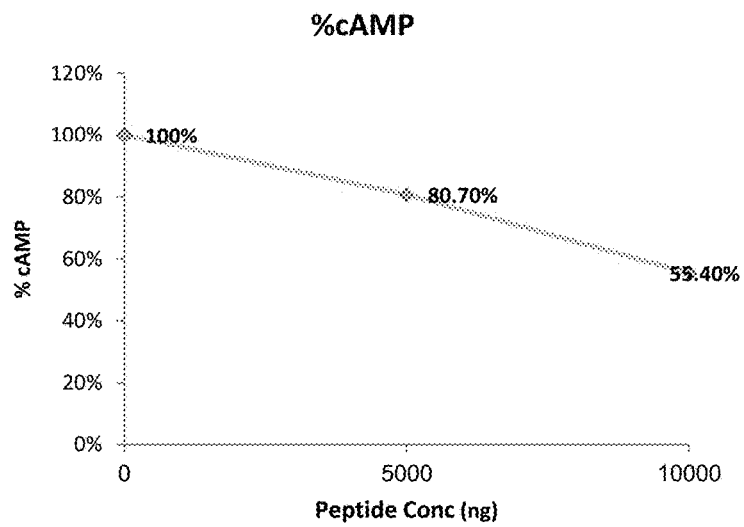
FIGS. 12A-B. cAMP ELISA binding assay. (12A) cAMP activated by the binding of the GNP+Peptide 1 to the DOR expressed on the C6 cells, in different dozes. (12B) Peptide 1 conjugated to GNP activated the cAMP regulation as affective as the peptide 1 (down to 80.70%).
Figure 12B:
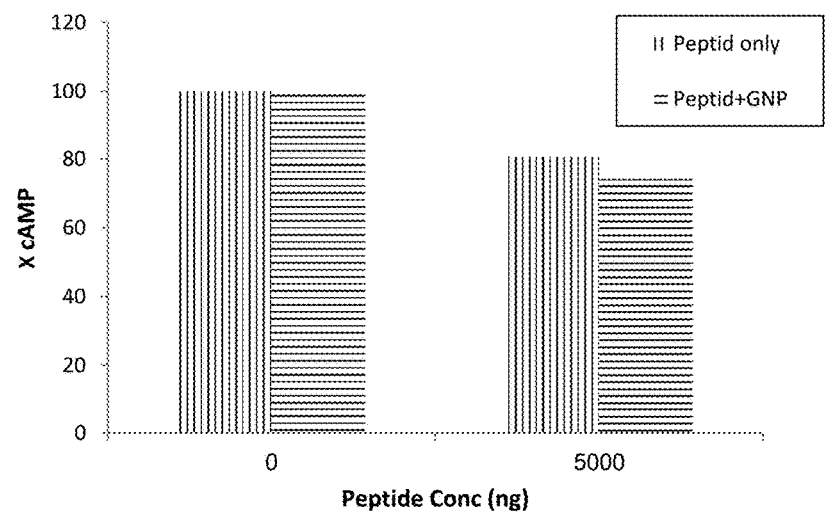

In order to assess the activity of the GNP conjugated to peptide 1, ELISA cAMP binding assay was conducted. The results demonstrated higher activity among the GNP conjugated to peptide 1 group as the cAMP binding was decreased to 80.70% from the initiation state (FIG. 12).

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An isolated peptide of less than 30 amino acid residues comprising the amino acid sequence as set forth in any one of:

(IIAGEYKQMLTL);    SEQ ID NO: 1
    and (NGNDRTDQMPLP);    SEQ ID NO: 2 or an analog thereof having (i) at least 80% sequence identity to said amino acid sequence and (ii) an increased binding affinity to delta (δ) opioid receptor.

2. The isolated peptide of claim 1, having a length of no more than 25 amino acids.

3. The isolated peptide of claim 1, having a length of no more than 20 amino acids.

4. The isolated peptide of claim 1, wherein said analog has at least 90% sequence identity to said amino acid sequence.

5. A pharmaceutical composition comprising as an active ingredient a pharmaceutically acceptable amount of the isolated peptide according to claim 1, and a pharmaceutically acceptable carrier.

6. The pharmaceutical composition of claim 5, further comprising a particle.

7. The pharmaceutical composition of claim 6, wherein said particle is a gold nanoparticle (GNP).

8. The pharmaceutical composition of claim 7, wherein said GNP is a PEGylated GNP.

9. The pharmaceutical composition of claim 7, wherein said isolated peptide is directly attached to said GNP.

10. The pharmaceutical composition of claim 8, wherein said isolated peptide is covalently linked to a functional group of said PEGylated GNP.

11. A method of treating or ameliorating a medical condition amenable to treatment with an opioid receptor agonist, the method comprising administering to a subject in need thereof the pharmaceutical composition of claim 5, thereby treating said medical condition in said subject, wherein said medical condition is selected from substance abuse addiction and pain.

12. The method of claim 11, wherein said opioid receptor agonist is a delta opioid receptor agonist.

13. The method of claim 11, wherein said substance is cocaine or a derivative thereof.

14. The isolated peptide of claim 1, wherein said peptide is a cyclized peptide.

* * * * *